United States Patent
Milczynski

(10) Patent No.: US 9,770,589 B2
(45) Date of Patent: Sep. 26, 2017

(54) ELECTRICAL COCHLEAR STIMULATION SYSTEM AND METHOD

(71) Applicant: ADVANCED BIONICS AG, Staefa (CH)

(72) Inventor: Matthias Milczynski, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 25 days.

(21) Appl. No.: 14/773,314

(22) PCT Filed: Mar. 6, 2013

(86) PCT No.: PCT/EP2013/054462
§ 371 (c)(1),
(2) Date: Sep. 4, 2015

(87) PCT Pub. No.: WO2014/135203
PCT Pub. Date: Sep. 12, 2014

(65) Prior Publication Data
US 2016/0015974 A1   Jan. 21, 2016

(51) Int. Cl.
*A61N 1/36* (2006.01)
*A61N 1/05* (2006.01)

(52) U.S. Cl.
CPC ....... *A61N 1/36032* (2013.01); *A61N 1/0541* (2013.01)

(58) Field of Classification Search
CPC ........ A61N 1/36032; A61N 1/36128–1/36196
See application file for complete search history.

(56) References Cited

U.S. PATENT DOCUMENTS

| | | | |
|---|---|---|---|
| 6,751,505 B1 | 6/2004 | Van Den Honert et al. | |
| 7,206,640 B1* | 4/2007 | Overstreet | A61N 1/36032 607/57 |
| 7,444,185 B1* | 10/2008 | Faltys | A61N 1/36032 607/137 |
| 2006/0052841 A1* | 3/2006 | Daly | A61N 1/08 607/57 |
| 2006/0235490 A1 | 10/2006 | Killian et al. | |
| 2011/0288613 A1 | 11/2011 | Smith et al. | |

FOREIGN PATENT DOCUMENTS

| WO | WO-01/74278 | 10/2001 |
|---|---|---|
| WO | WO-2009/143553 | 12/2009 |
| WO | WO-2011/032021 | 3/2011 |

OTHER PUBLICATIONS

International Search Report and Written Opinion received in International Application No. PCT/EP2013/054462, dated Oct. 2, 2013.

(Continued)

*Primary Examiner* — Michael Kahelin
(74) *Attorney, Agent, or Firm* — ALG Intellectual Property, LLC

(57) ABSTRACT

A system includes means for providing an input audio signal; a sound processor for generating an electric stimulation signal from the input audio signal; and a cochlear implant electrode arrangement comprising a plurality of stimulation channels for stimulating the cochlea according to the electric stimulation signal.

4 Claims, 9 Drawing Sheets

(56) References Cited

OTHER PUBLICATIONS

Arnold, et al., "Neural response imaging (NRI) cochlear mapping: prospects for clinical application", *Database Medline, US National Library of Medicine (NLM)*, Dec. 2007, XP002712944, Database accession No. NLM18033738.
C. Van Den Honert, et al., "Focused intracochlear electric stimulation with phased array channels", *J. Acoust. Soc. Am.* 121 (6), 2007, pp. 3703-3716.
D. Van Compernolle, "Speech processing strategies for a multichannel cochlear prosthesis", *PhD Thesis, Stanford University*, 1985.
K. L. Rodenhiser, et al., "A method for determining the driving currents for focused stimulation in the cochlea", *IEEE Trans Biomed Eng*, vol. 42 (4), 1985, pp. 337-342.
J. H. M. Frijns, et al., "Neural excitation patterns induced by phased-array stimulation in the implanted human cochlea", *Acta Oto-Laryngologica*, 131, 2011, pp. 362-370.
Nogueira, et al., "A psychoacoustic "NofM"-type speech coding strategy for cochlear implants", *EURASIP J. Appl. Signal Process.*, vol. 18, 2005, pp. 3044-3059.

\* cited by examiner

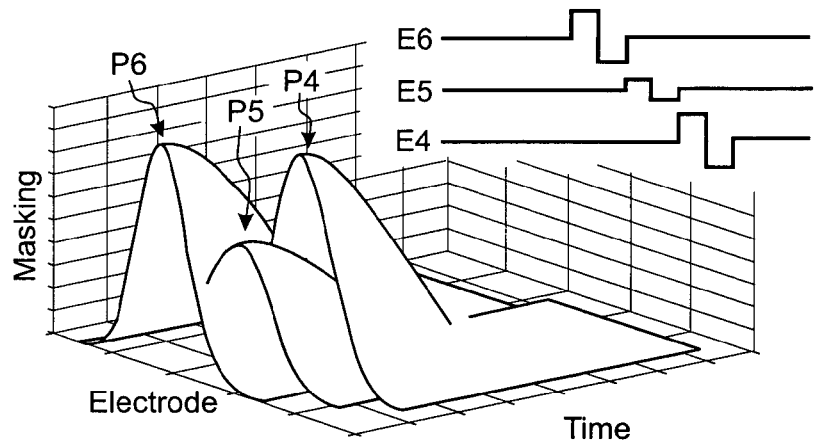
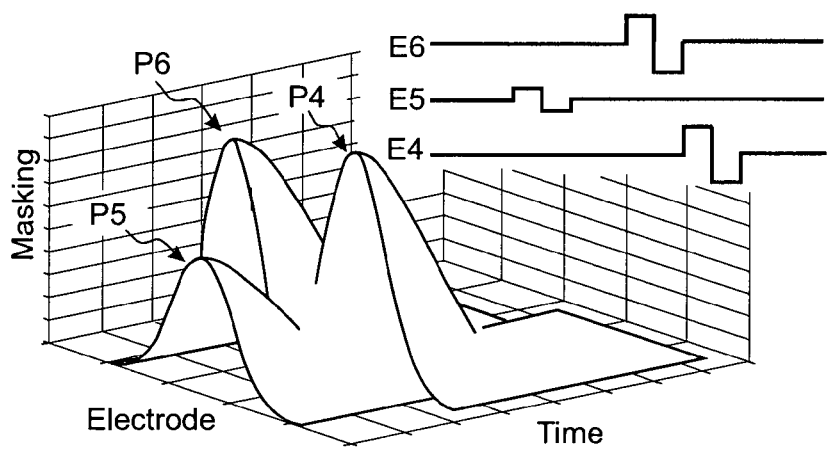
FIG. 9
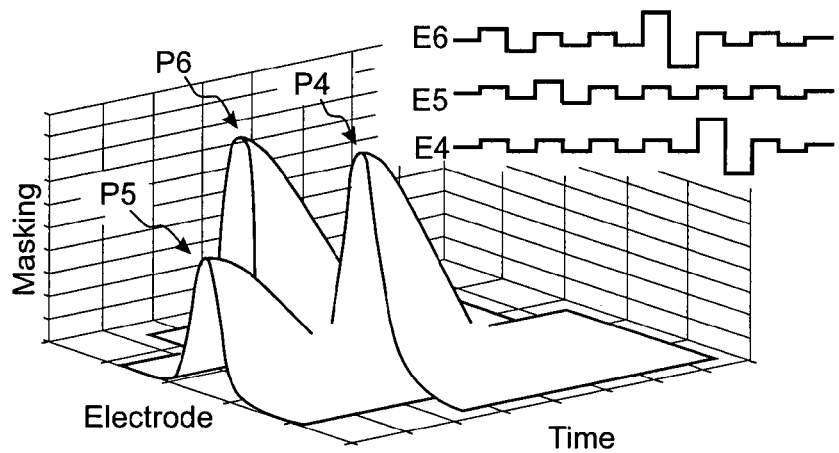

ELECTRICAL COCHLEAR STIMULATION SYSTEM AND METHOD

The invention relates to a system and a method for electrical stimulation of a patient's cochlea.

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant (CI) systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, which usually is captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals in each stimulation channel is generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to stimulate a stimulation site located in between areas associated with two or more electrodes) and n-of-n stimulation (wherein stimulation current is only applied to n of in total stimulation channels during a particular stimulation frame).

An example for such a CI system with electrical cochlea stimulation is described in WO 2011/032021 A1.

Currently, continuous-interleaved stimulation, i.e. time-interleaved stimulation of successive channels, is the typically preferred choice of delivering electric pulses with CI devices. Significant reduction in channel interaction and a safer stimulation compared to analog stimulation are the main benefits of this approach.

In monopolar stimulation, which is the standard stimulation mode in state-of-the-art CI devices, an extra cochlea electrode serves as the ground electrode. Bipolar stimulation was introduced as an alternative, wherein a near-by-electrode is activated simultaneously with the stimulating electrode at the same current amplitude, but with opposite phase. Recently, more complex stimulation modes were proposed to implement so-called "current focusing". The current focusing approach aims at providing a tonotopically (or spatially) narrower excitation, leading to reduced spread-of-excitation (SOE). Such multipolar stimulation modes include tripolar stimulation and phased-array stimulation. In tripolar stimulation the current delivered by one stimulation electrode is compensated by both neighboring electrodes, each of which delivers half of the currents of the stimulating electrode at an opposite phase. In phased-array stimulation, the current of the stimulating electrode is compensated by all the other electrodes, with the weights for the compensating currents being obtained by neural response imaging based impedance measures.

Some CI systems utilize a so-called pulse table concept in the implantable cochlear stimulator (ICS) component wherein e.g. the order of the stimulating electrodes is fixed for each stimulation cycle (a stimulation cycle refers to one time-interleaved sequence of biphasic pulses which codes a single frame of the input signal at hand). During one stimulation cycle, either each electrode is activated once, a subset of electrodes is activated ("n-of-m" strategy), or pairs of neighboring electrodes are activated (e.g. "current steering").

Examples of phased-array stimulation in CI devices can be found in US 2011/0288613 A1 and in the article "Focused intracochlear electric stimulation with phased array channels" by C. van den Honert et al., J. Acoust. Soc. Am. 121 (6), 2007, pages 3703-3716. In US 2011/0288613 A1 a simple mathematical model is proposed for obtaining stimulation currents for each electrode corresponding to a desired voltage profile, with each current values having been deduced from impedance measures recorded from intracochlear responses, wherein subject-specific transimpedance matrices (spreading functions) were employed.

Earlier work on this field is described in D. van Compernolle "Speech processing strategies for a multi-channel cochlear prosthesis", PhD Thesis, Stanford University, 1985, the article "Reduction of electrically interaction in auditory prostheses", by B. Townsend et al., in IEEE Trans Biomed Eng, vol. 34 (11), 1987, pages 891-897, and the article "A method for determining the driving currents for focused stimulation in the cochlea", by K. L. Rodenhiser et al., IEEE Trans Biomed Eng, vol. 42 (4), 1985, pages 337-342.

In the article "Neural excitation patterns induced by phased-array stimulation in the implanted human cochlea", by J. H. M. Frijns et al., in Acta Oto-Laryngologica, 131, 2011, pages 362-370, a model is shown according to which a narrower neural excitation is achieved using phased-array stimulation.

U.S. Pat. No. 6,751,505 B1 relates to a CI system, wherein the latency is measured via neural response telemetry and is used for determining stimulation parameters such as stimulation rate, electrode selection, number of stimulation channels, stagger order (i.e. the sequence with which electrodes are selected for stimulation) and tuning of high-rate conditional pulse-trains.

The article "A psychoacoustic "NofM"-type speech coding strategy for cochlear implants" by W. Nogueira et al., in EURASIP J. Appl. Signal Process., vol. 18, 2005, pages 3044-3059, relates to a CI coding strategy utilizing triangular SOE curves typically used in the mp3 coding standard for determining the selection of stimulation channels within an n-of-m selection; it was demonstrated that with a corresponding 4-of-22 selection similar speech recognition course can be obtained compared to a standard ACE (advanced combinational encoder) strategy with an 8-of-22 selection.

WO 2009/143553 A1 relates to a CI coding strategy using subject-specific psychophysical as well as physiological measures, such as electrically evoked compound action potentials (eCAPs), for determining the population of excitable neurons close to stimulating electrodes. Such measures were used to weight the spectral components of the input signal at hand, thereby determining, for each biphasic pulse, the precise timing, the stimulating electrode to be used, and the current level; also phased-array stimulation is mentioned.

It is an object of the invention to provide for an electrical cochlear stimulation system and method allowing for improved frequency resolution that may, among others, also lead to improved pitch perception.

According to the invention, this object is achieved by the systems and methods described herein.

The invention is beneficial in that, by considering patient-specific forward masking patterns obtained from patient-specific neural response imaging data in the selection of the temporal stimulation order of the stimulation channels according to a patient-specific pulse table in a manner so to minimize spatial and/or temporal masking of the stimulation signal according to an optimization algorithm, channel interaction and SOE is minimized, thereby enhancing pitch perception by the patient (enhanced pitch perception is particularly useful for music listening, speaker segregation, timbre and tonal language perception). In particular, the patient's frequency resolution can be enhanced.

The present invention is particularly effective in conjunction with a phased-array stimulation strategy.

Preferably, the patient-specific neural response imaging data are eCAP data.

According to one embodiment, the sound processor may use a fixed or static pulse table, i.e. a pulse table which is constant in time. According to a more sophisticated approach, the pulse table may be regularly updated as a function of the spectral characteristic of the input audio signal, with the spectral characteristic being determined by the signal levels of the analysis channels relative to each other, thereby resulting in a dynamic pulse-table.

Further preferred embodiments are defined in the dependent claims.

Hereinafter, examples of the invention will be illustrated by reference to the attached drawings, wherein:

FIG. 9 is a representation similar to FIGS. 7 and 8, wherein, however, the masking potential at each electrode is shown as a function of time; a comparative example according to the prior art is shown at the top, an example of biphasic stimulation is shown in the middle and an example of biphasic phased-array stimulation is shown at the bottom of FIG. 9.

Figure 1:
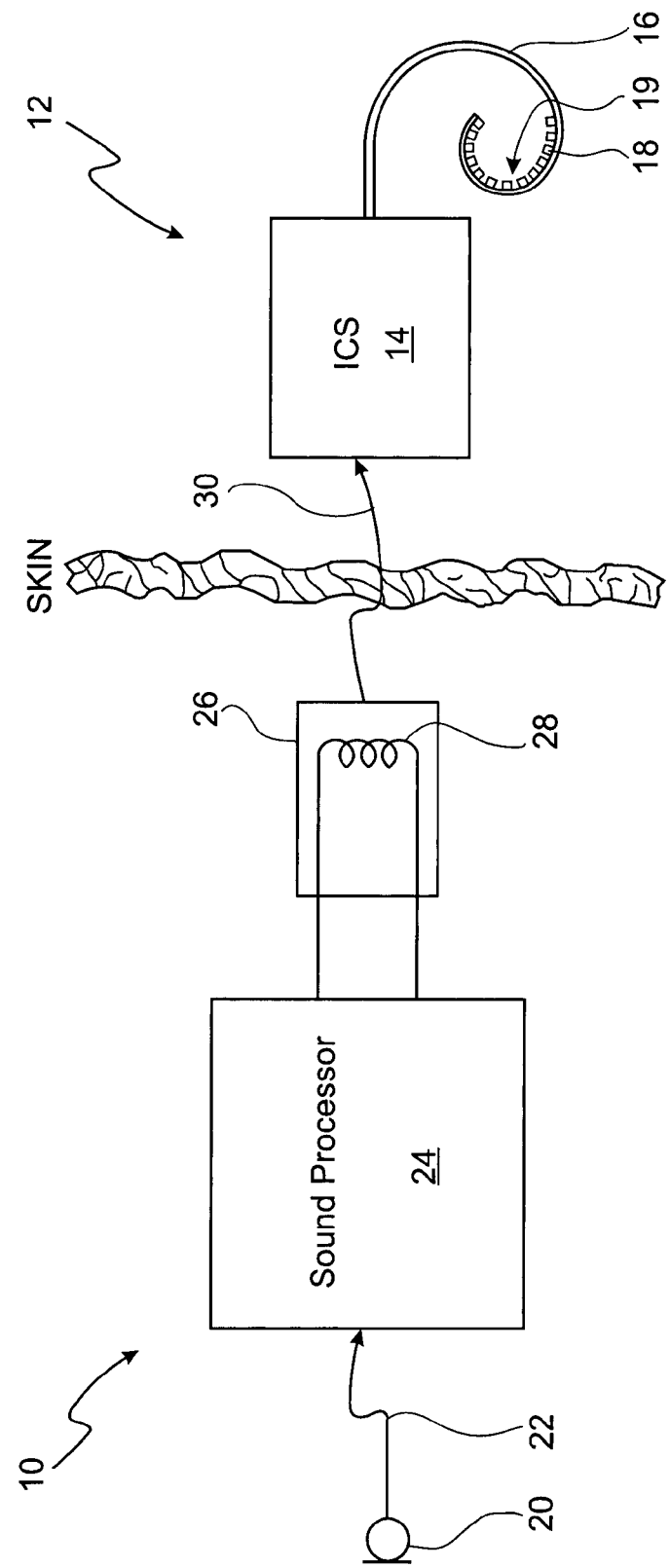
FIG. 1 is a schematic representation of an example of a CI system according to the invention.

In FIG. 1 an example of a cochlear implant system is shown schematically. The system comprises a sound processing sub-system 10 and a stimulation sub-system 12. The sound processing sub-system 10 serves to detect or sense an audio signal and divide the audio signal into a plurality of analysis channels each containing a frequency domain signal (or simply "signal") representative of a distinct frequency portion of the audio signal. A signal level value is determined for each analysis channel by analyzing the respective frequency domain signal Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlear of a patient in accordance with the stimulation parameters received from the sound processing sub-system 10. Electrical stimulation is provided to the patient via a CI stimulation assembly 18 comprising a plurality of stimulation channels, wherein various known stimulation strategies, such as current steering stimulation or N-of-M stimulation, may be utilized.

As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes.

As used herein, an "n-of-m stimulation strategy" is one in which stimulation current is only applied to n of m total stimulation channels during a particular stimulation frame, where n is less than m. An n-of-m stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), duty cycle, spectral tilt, ramp on time, and ramp off time of the stimulation current that is applied to the stimulation site.

Figure 2:
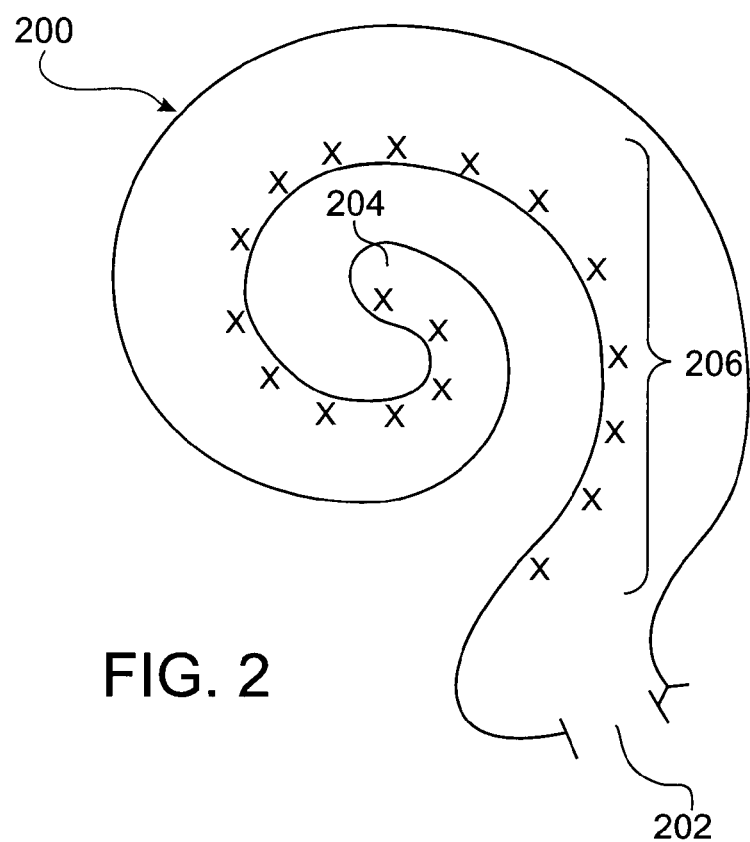
FIG. 2 is a schematic cross-sectional view of a human cochlea with marked stimulation sites.

FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 1, sound processing subsystem 10 and stimulation subsystem 12 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 1, the stimulation subsystem 12 comprises an ICS 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 1, the sound processing sub-system 10 is designed as being located external to the patient; however, in alternative examples, at least one of the components of the sub-system 10 may be implantable.

In the example shown in FIG. 1, the sound processing sub-system 10 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 1 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 3:
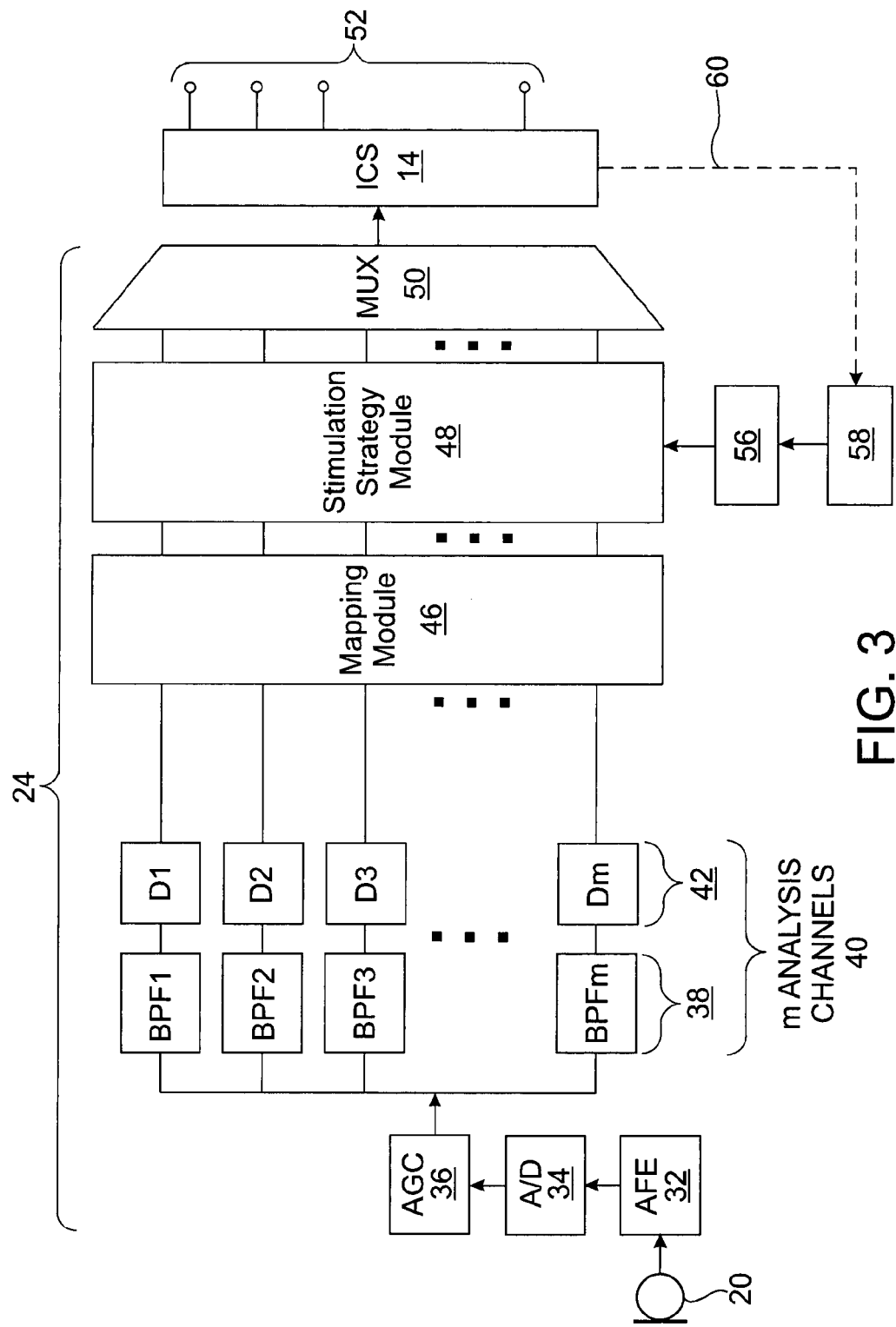
FIG. 3 is a block diagram of an example of the signal processing structure of a CI system according to the invention.

In FIG. 3 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then divide the resulting frequency bins into the analysis channels 40.

The signals within each analysis channel 40 are input into an envelope detector 42 in order to determine the amount of energy contained within each of the signals within the analysis channels 40 The output signals of the envelope detectors 42 are supplied to a mapping module 46 which serves to map the signals in the analysis channels 40 to the stimulation channels S1 . . . Sn. For example, signal levels may be mapped to amplitude values used to define the electrical stimulation pulses that are applied to the patient by the ICS 14 via M stimulation channels 52. For example, each of the in stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter, such as the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values and/or filter characteristics. Examples of such auditory prosthesis devices, as described so far, can be found, for example, in WO 2011/032021 A1.

The stimulation strategy module 48 uses time-interleaved stimulation according to a pulse table provided by a pulse table configuration module 56. The pulse table configuration module 56 generates a patient-specific pulse table from patient-specific forward masking patterns obtained from patient specific neural response imaging data provided by a unit 58 to the pulse table configuration module 56. The pulse table is re-configured based on the patient's specific forward masking patterns in a manner so as to minimize spatial and/or temporal masking of the stimulation signal according to an optimization algorithm implemented in the pulse table pulse table configuration module 56.

Figure 6:
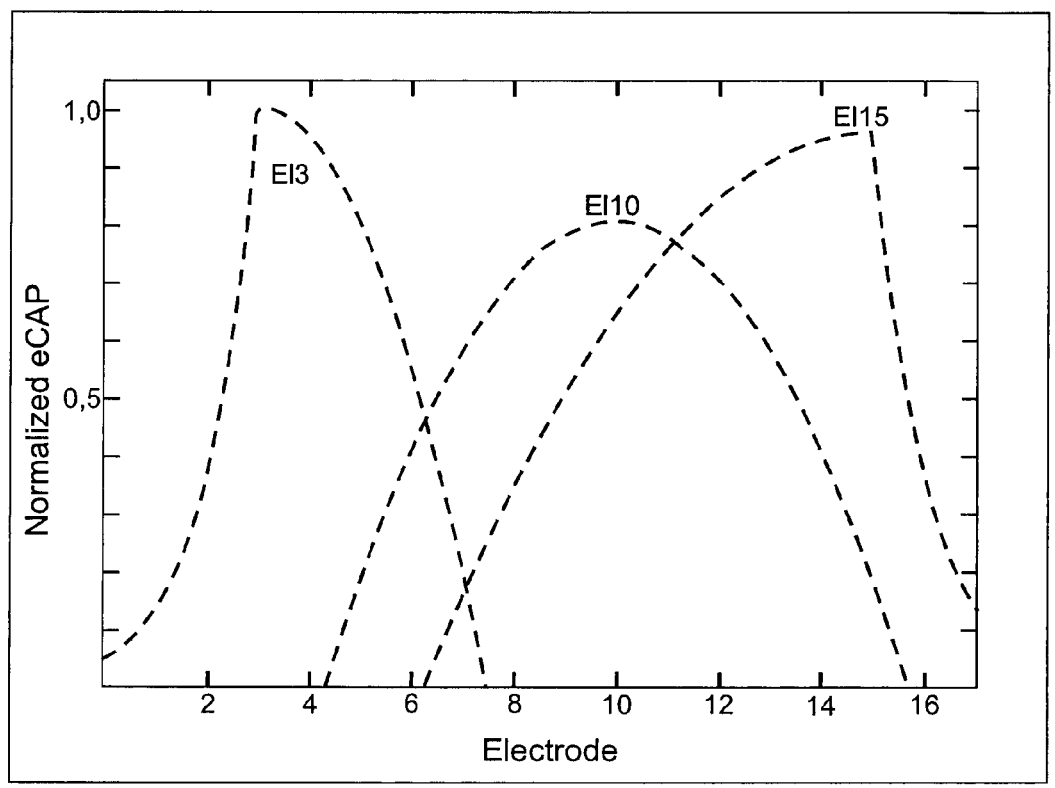
FIG. 6 is an example of eCAP data to be used in a CI system according to the invention.

According to a preferred embodiment, the patient specific neural response imaging data are eCAP data obtained by reverse telemetry from the electrodes 19 and the ICS 14 via the transcutaneous link 30 (this path is indicated in FIG. 3 at 60). A schematic example of such eCAP data in the spatial domain (spreading functions) is shown in FIG. 6 wherein the masking effect of the electrodes #3 (EL3), #10 (EL10) and #15 (EL15) with regard to the other electrodes are shown. As can be seen in FIG. 6, masking curves typically vary considerably across probe locations. Further, apical portions of the curves may differ from basal portions, i.e. the masking patterns are not symmetric around the probe location.

Figure 7:
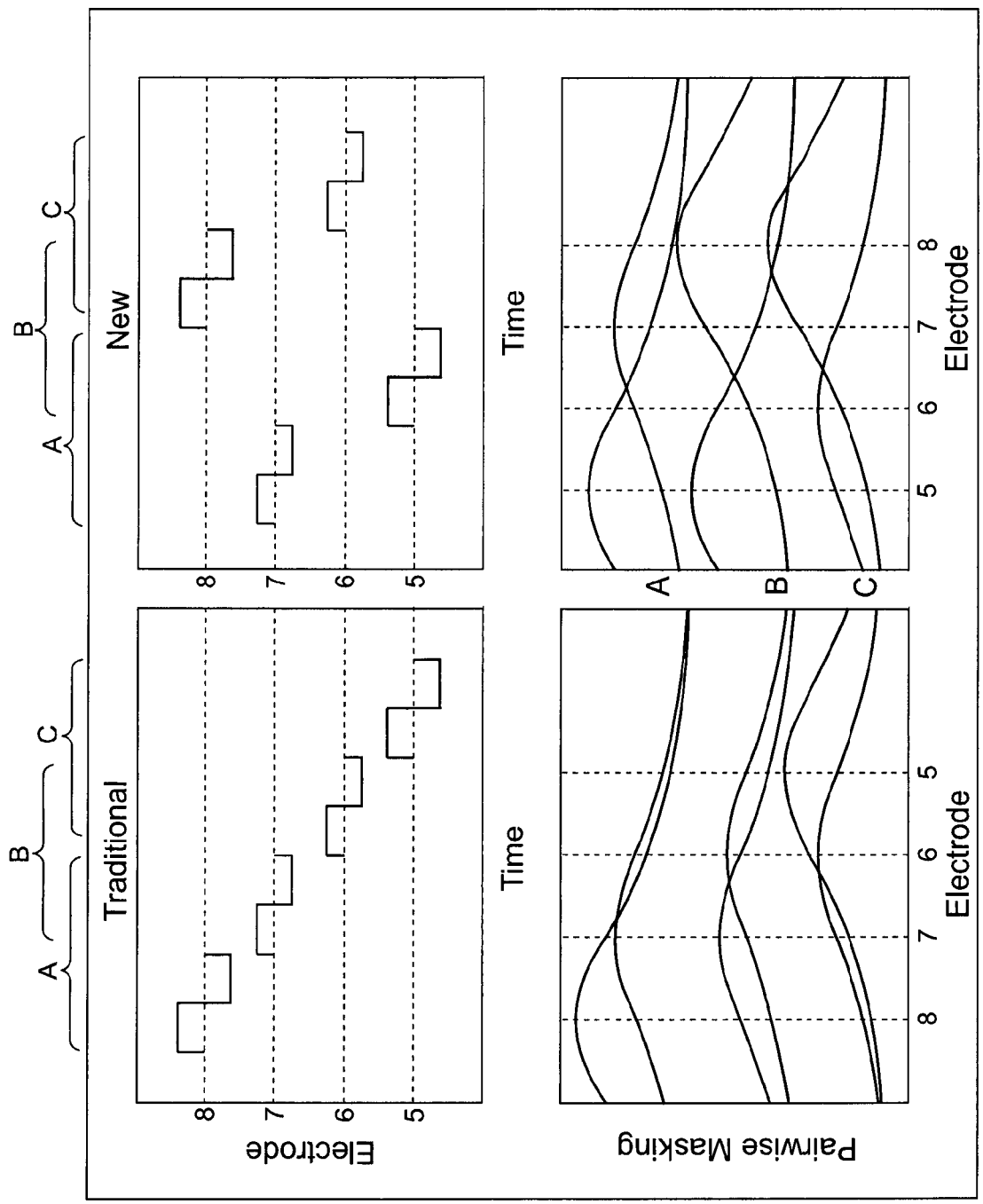
FIG. 7 is a schematic example of the stimulation pattern with biphasic pulses (upper part) and the respective pair-wise masking (lower part), wherein the example according to the invention is shown at the right-hand side and a comparative example according to the prior art is shown at the left-hand side.

An example of a masking-optimized stimulation strategy is illustrated in FIG. 7 for monopolar stimulation with biphasic pulses. At the bottom of FIG. 7, the stimulation current at the electrodes number 5 to 8 is shown versus time. The left-hand part of FIG. 7 shows a conventional stimulation strategy, wherein the electrodes are simply stimulated one after the other during each stimulation cycle (starting with electrode #8 and terminating with electrode #5). Simulations of the resulting pairwise masking patterns elicited by two successive electrode pairs are shown at the bottom of FIG. 7 (the electrode pairs are distinguished in the representation of the masking pattern by different vertical off-set). It can be seen that the successive electrode stimulation according to the conventional stimulation strategy results in significant pairwise masking of biphasic pulses.

The right-hand side of FIG. 7 shows a corresponding illustration of a stimulation strategy taking into account patient specific forward masking patterns. Based on the patient specific forward masking patterns an optimization algorithm is used for finding an electrode stimulation sequence providing for the least spatial forward masking across all biphasic pulses. Such optimization process may be enhanced by incorporating information on recovery functions which may also be obtained from patient specific measurements; recovery functions determine the degree of temporal masking of a single pulse. Thus, by taking into account also recovery functions, the resulting optimization process is able to both minimize spatial and temporal masking.

In the example of FIG. 7, the masking-optimized stimulation sequence (electrode #7, #5, #8 and #6) results in reduced spatial pairwise masking, which is achieved by the spatial (i.e. tonotopical) separation of successive pulses, as opposed to the conventional stimulation order.

In the most simple case, the pulse table is configured to be static, i.e. the same electrode stimulation order is used in all stimulation cycles. While such approach is computationally less demanding, a still further reduced spatial and/or temporal masking may be achieved by taking into account also the spectral shape of the input signal (the reason is that the strength of masking of a biphasic pulse also depends on the magnitude of the pulse). Such a dynamic or time-varying pulse table is updated (or re-configured) as a function of the spectral characteristic of the input audio signal (the spectral characteristic is determined by the signal level of the analysis channel 40 relative to each other as determined by the filter bank 38 and the envelope detector 42). Such update preferably occurs for each new stimulation cycle.

Figure 4:
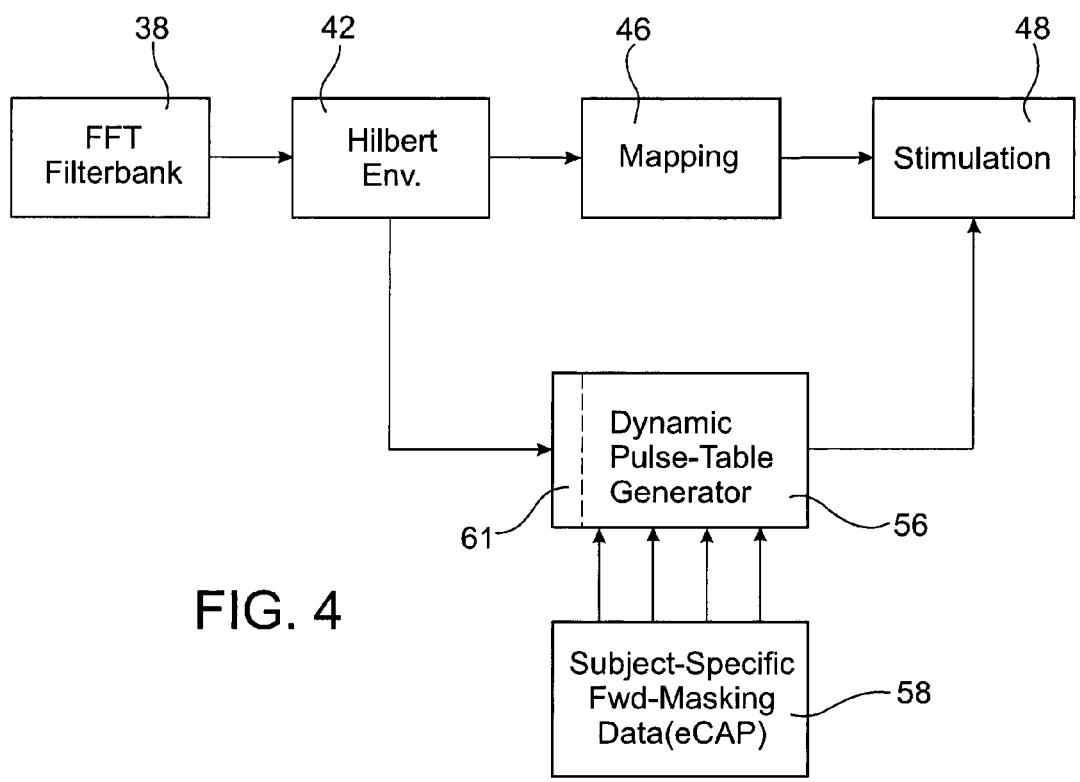
FIG. 4 is a schematic block diagram of an example of the signal processing structure of a CI system according to the invention employing a dynamic pulse table.
Figure 5:
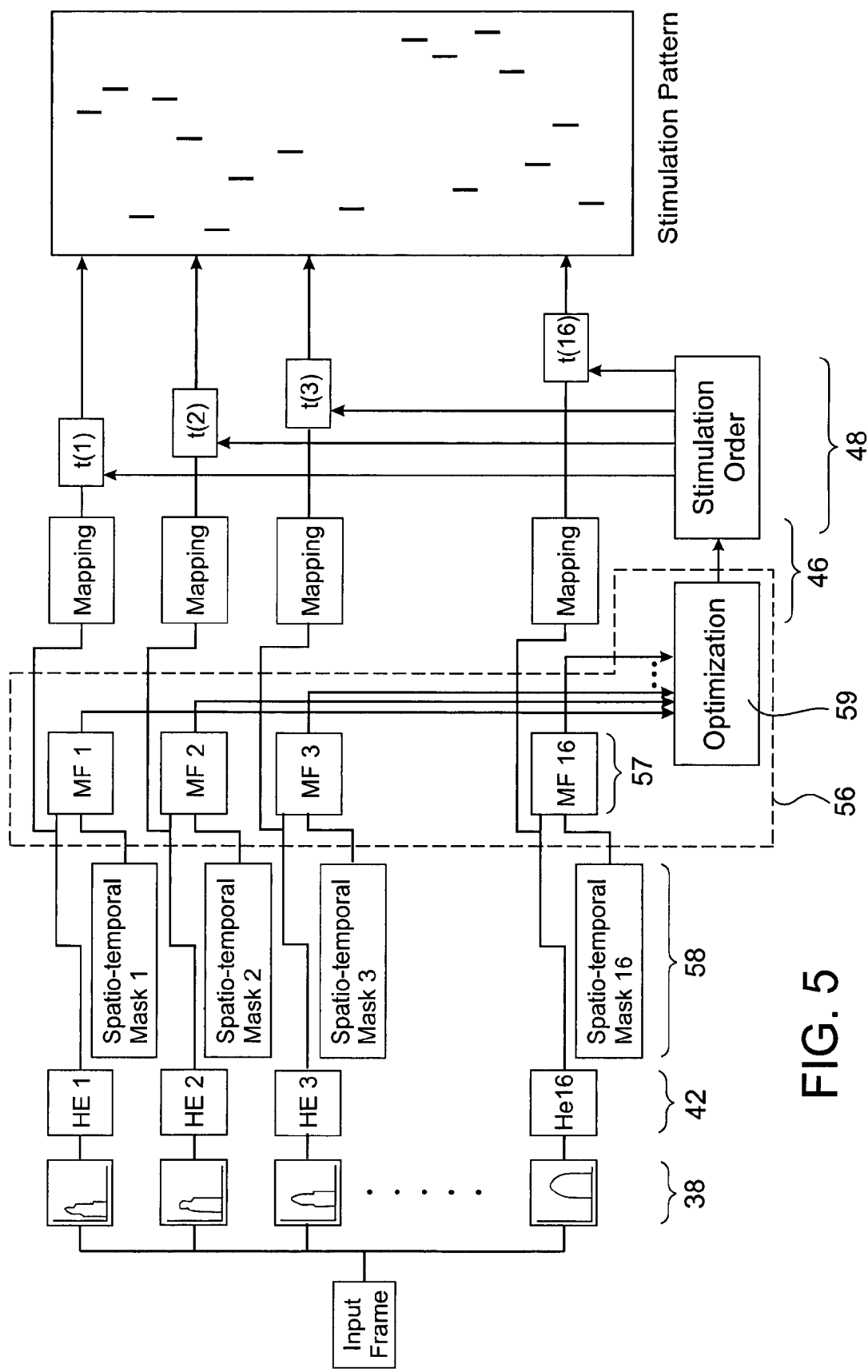
FIG. 5 is another example of a block diagram of a signal processing structure of a CI system according to the invention.

An example of an implementation of such dynamic pulse table is illustrated in FIGS. 4 and 5. According to FIG. 4, the output of the (Hilbert) envelope detectors 42 is supplied not only to the mapping module 46 but also to the pulse table configuration module 56, so that the pulse table can be updated for each stimulation cycle according to the present spectral characteristic of the input audio signal as detected by the envelope detector 42.

FIG. 5 is a more detailed representation of the processing scheme of FIG. 4, wherein 16 analysis channels and 16 stimulation channels are illustrated. For each stimulation channel/electrode spatio-temporal masking data 58 are supplied, together with the respective output of the envelope detector 42 of the same channel, to a masking function unit 57 which provides for an output to an optimization unit 59 of the pulse table configuration module 56, which output is indicative of the actual masking action of the respective electrode for the present signal level of the same (analysis) channel.

The optimization algorithm may be a direct search algorithm or an evolutionary algorithm, such as a genetic algorithm. Also, models inspired by signal detection theory may be used.

Since the implementation of a dynamic pulse table requires relatively large computational efforts, resulting in a corresponding high power consumption, the pulse table configuration module 56 may vary the content of the pulse table only in case that the input signal is a voiced/speech signal or a music signal, for which a certain degree of harmonicity is given. To this end, the sound processor 24 may comprise a classifier (indicated at 61) for determining whether there is a voiced or unvoiced signal by determining the degree of harmonicity of the input audio signal, wherein the pulse table configuration module 56 is controlled according to the output of the classifier 61. During times when no voice or music input signal is detected, the pulse table configuration module may use a static pulse table.

The stimulation strategy applied by the module 48 may be such that the number of selected pulses may vary across the stimulation cycles, i.e. an n-of-m type algorithm may be used. Further, the stimulation strategy may be used in conjunction with current steering.

Figure 8:
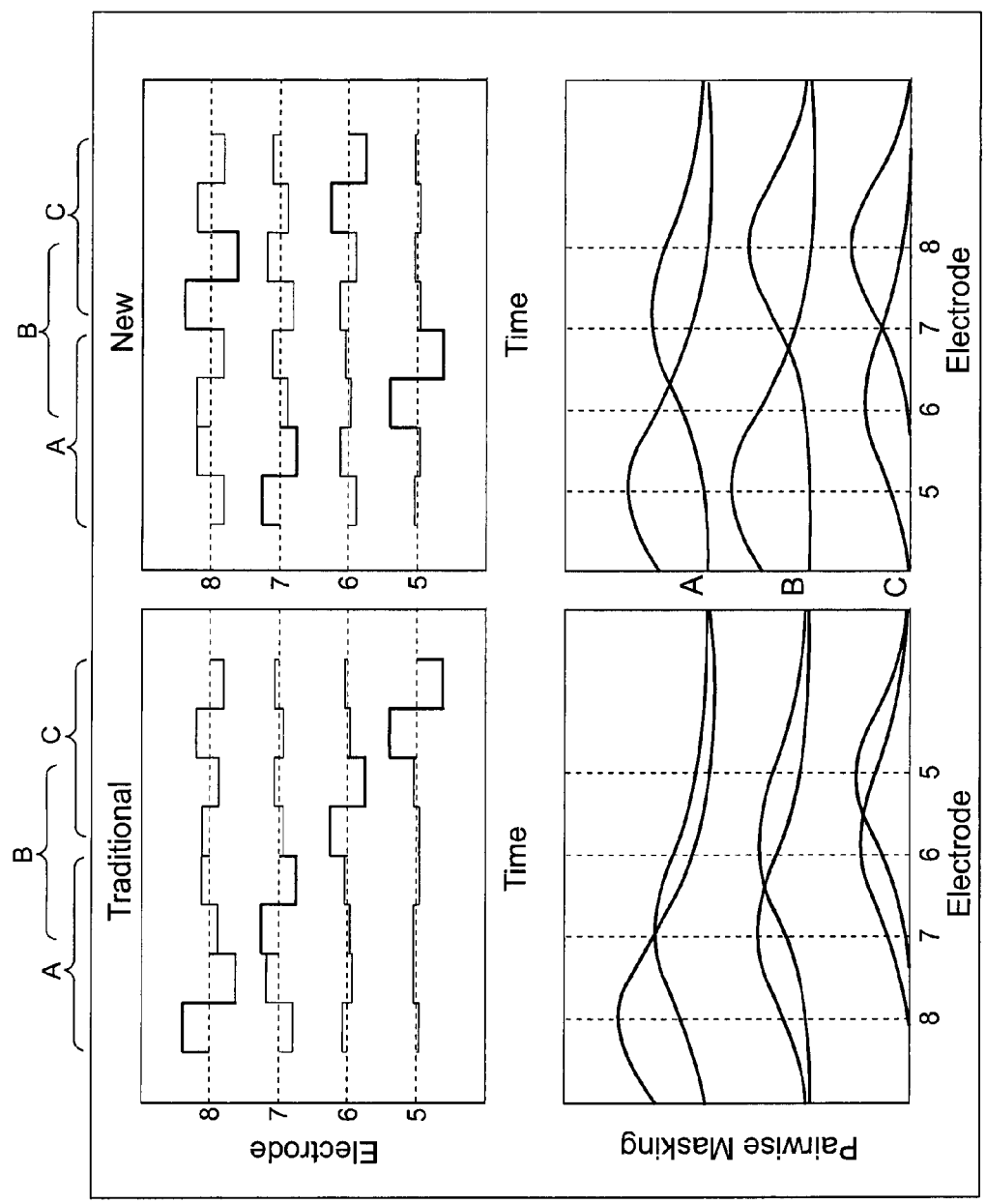
FIG. 8 is a view like FIG. 7, however, for phased-array biphasic pulses.

While the present invention may be used with monopolar, biphasic stimulation, as shown in FIG. 7, it is preferably used for multipolar stimulation, in particular for phased-array stimulation. A schematic example of phased-array stimulation is illustrated in FIG. 8, wherein at the left-hand side a comparative example using a conventional stimulation order (corresponding to the comparative example at the left-hand side of FIG. 7) and at the right-hand side an example using a masking-optimized stimulation order (corresponding to the example of the right-hand side of FIG. 7) is shown. It can be seen from the simulations shown at the bottom of FIG. 8 that the pairwise masking obtained for the phased-array stimulation is less than that obtained with the monopolar stimulation example shown at the right-hand side of FIG. 7.

FIG. 9 is a further illustration of the spatio-temporal masking for three adjacent electrodes E4, E5 and E6 for conventional time-interleaved stimulation order (top), for masking-optimized stimulation order for monopolar biphasic stimulation (center), and for masking-optimized stimulation order for biphasic phased array stimulation (bottom). It can be seen, as in FIGS. 7 and 8, that the masking optimized stimulation order using phased array stimulation provides for the least masking and most focused stimulation, whereas with the conventional ordering, for example, the pulse P5 is entirely masked.

The invention claim is:

1. A system for electrical stimulation of a patient's cochlea, comprising:
   means for providing an input audio signal;
   a sound processor configured to generate an electric stimulation signal from the input audio signal; and
   a cochlear implant electrode arrangement comprising a plurality of stimulation channels and configured to stimulate the cochlea according to the electric stimulation signal;
   the sound processor comprising
      a filter-bank unit configured to divide the input audio signal into a plurality of analysis channels, each analysis channel in the plurality of analysis channels containing a frequency domain signal representative of a distinct frequency portion of the audio signal,
      a signal level unit configured to determine a signal level for each analysis channel by analyzing the respective frequency domain signal,
      a stimulation signal unit configured to generate an electric stimulation signal for each stimulation channel according to the respective signal level,
      a pulse table configuration module configured to generate a patient-specific pulse table from forward masking patterns specific to the patient and obtained from neural response imaging data specific to the patient,
      a stimulation order control unit configured to control a temporal stimulation order of the stimulation channels according to the patient-specific pulse table,
      a classifier unit configured to determine whether the input audio signal is a voiced signal or an unvoiced signal, and the pulse table configuration module being controlled by the classifier unit such that the pulse table configuration module provides a static pulse table that is used as the patient-specific pulse table if the classifier unit determines that the input audio signal is the unvoiced signal and a dynamic pulse table that is used as the patient-specific pulse table and that is updated as a function of a spectral characteristic of the input audio signal if the classifier unit determines that the input audio signal is the voiced signal.

2. The system of claim 1, wherein the classifier unit is configured to determine a degree of harmonicity of the input audio signal in order to determine whether the input audio signal is the voiced signal or the unvoiced signal.

3. The system of claim 1, wherein the neural response imaging data includes eCAP data.

4. The system of claim 1, wherein the electric stimulation signal is a current steering stimulation signal.

* * * * *